United States Patent
Isabelle

(10) Patent No.: US 9,585,791 B2
(45) Date of Patent: Mar. 7, 2017

(54) LENS FOR PROTECTION OF ONE OR MORE EYES OF A USER, METHOD OF DESIGNING EYEWEAR, AND METHOD OF MANUFACTURING EYEWEAR

(71) Applicant: Fosta-Tek Optics, Leominster, MA (US)

(72) Inventor: Paul Isabelle, St-Augustin-de-Desmaures (CA)

(73) Assignee: I-DESIGN (9045-6278 QUEBEC INC.), Saint-Augustin-de-Desmaures, QC (CA)

( * ) Notice: Subject to any disclaimer, the term of this patent is extended or adjusted under 35 U.S.C. 154(b) by 597 days.

(21) Appl. No.: 14/073,482

(22) Filed: Nov. 6, 2013

(65) Prior Publication Data
US 2015/0121611 A1 May 7, 2015

(51) Int. Cl.
*G02C 7/02* (2006.01)
*A61F 9/02* (2006.01)
*A42B 3/04* (2006.01)
*G02C 7/06* (2006.01)

(52) U.S. Cl.
CPC ............... *A61F 9/02* (2013.01); *A42B 3/042* (2013.01); *G02C 7/022* (2013.01); *G02C 7/068* (2013.01); *Y10T 428/24479* (2015.01); *Y10T 428/24488* (2015.01)

(58) Field of Classification Search
CPC ........ G02C 7/022; G02C 7/028; G02C 7/068; G02C 2202/04; G02C 2202/06; G02C 2202/12; A42B 3/042; A42B 3/06; A42B 3/062; A42B 3/22; F41H 1/04

USPC ....... 351/44, 159.01, 159.71, 159.72, 159.73
See application file for complete search history.

(56) References Cited

U.S. PATENT DOCUMENTS

| | | | |
|---|---|---|---|
| 5,774,201 A | 6/1998 | Tackles | |
| 5,825,455 A | 10/1998 | Fecteau et al. | |
| 5,909,267 A | 6/1999 | Hall et al. | |
| 6,364,481 B1 | 4/2002 | O'Connor et al. | |
| 7,389,543 B2 | 6/2008 | Reichow et al. | |
| 7,407,283 B2 | 8/2008 | Babineau et al. | |
| 7,419,261 B2 | 9/2008 | Dumange et al. | |
| 7,717,559 B2 | 5/2010 | Ito et al. | |
| 7,784,937 B2 | 8/2010 | Keane et al. | |
| 8,002,406 B2 | 8/2011 | Arrigotti et al. | |
| 8,310,481 B2 | 11/2012 | Bailey | |
| 8,340,799 B2 | 12/2012 | Hagen et al. | |
| 2007/0058130 A1 | 3/2007 | Babineau et al. | |
| 2008/0074610 A1* | 3/2008 | Tackles ................. G02C 7/02 351/159.01 |

FOREIGN PATENT DOCUMENTS

CA 2225823 11/1997
WO WO9721139 6/1997

* cited by examiner

*Primary Examiner* — Huy K Mai
(74) *Attorney, Agent, or Firm* — Welsh Flaxman & Gitler LLC

(57) ABSTRACT

Some embodiments concern a lens for protection of one or more eyes of a user. The lens can include: a first surface; and a second surface spaced apart from the first surface such that the lens has a variable thickness between the first surface and the second surface. The first surface can include substantially an arc. The second surface can include a substantially elliptical curve and the lens can be a smooth, arcuate, substantially plano lens. Other embodiments are disclosed.

14 Claims, 16 Drawing Sheets

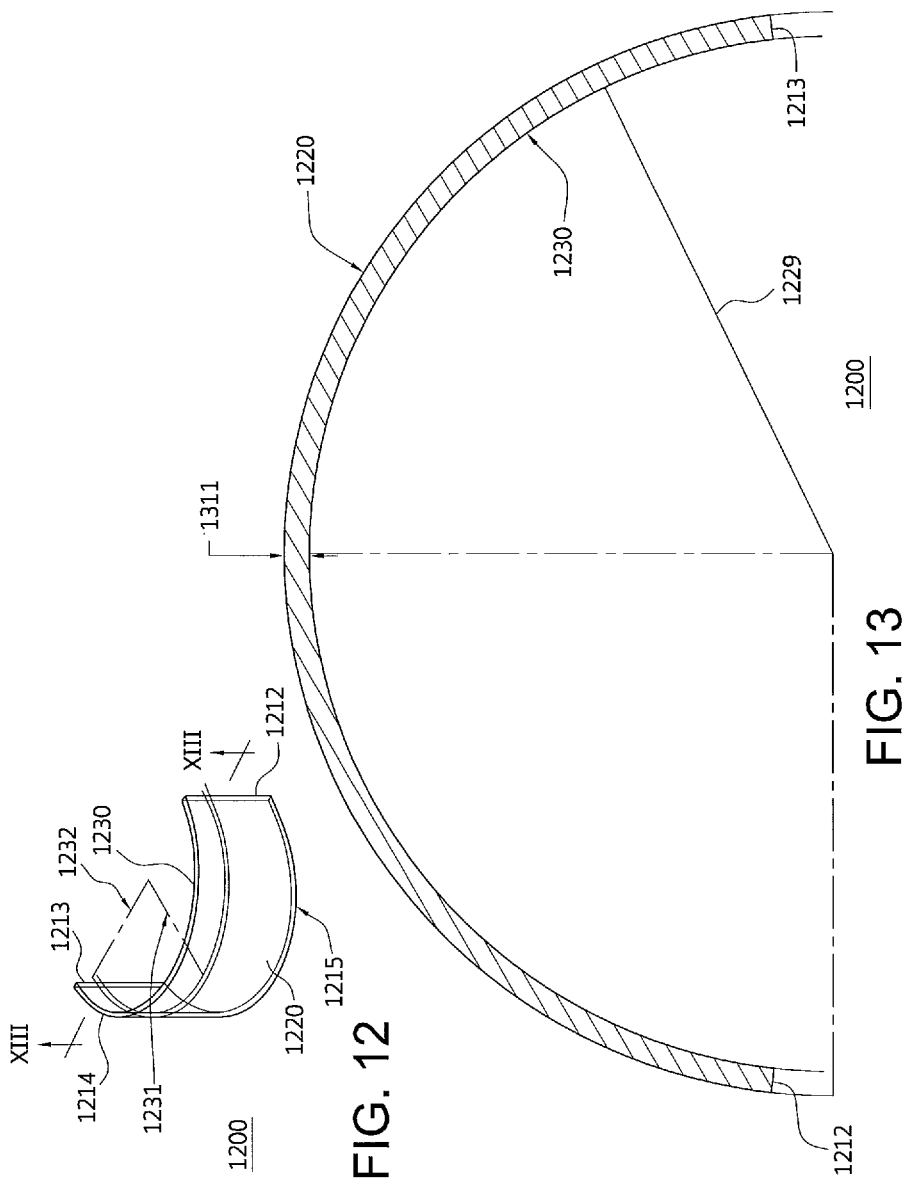

OPTICAL PROPERTIES OF A TYPICAL ELLIPTICALLY CORRECTED ARCUATE LENS

Example: CYLINDRICAL LENS, 100.00mmR, 6.00mm nominal thickness, IPD 64mm.

| Thickness | CONSTANT THICKNESS | "Optically Correct" | | Elliptical 1 | | Elliptical 2 | |
|---|---|---|---|---|---|---|---|
| Center | 6.00 | 6.00 | | 6.00 | | 6.00 | |
| Edge | 6.00 | | | | | 6.00 | |
| Thinnest | 6.00 | | | | | 4.98 | excellent |
| | | FAILS IMPACT REQUIREMENTS | | | | | |
| Forward Gaze Criteria (ex: ANSI Z87.1) | | | | | | | |
| Power +/-0.06D | | 0.00 | PASS | 0.00 | PASS | 0.00 | PASS |
| Astigmatism +/-0.06D | | 0.00 | PASS | 0.00 | PASS | 0.00 | PASS |
| Prism 0.25D | | 0.03 | PASS | 0.02 | PASS | 0.03 | PASS |
| IMB 0.50D | | 0.06 | PASS | 0.04 | PASS | | |

FIG. 18

LENS FOR PROTECTION OF ONE OR MORE EYES OF A USER, METHOD OF DESIGNING EYEWEAR, AND METHOD OF MANUFACTURING EYEWEAR

FIELD OF THE INVENTION

This invention relates generally to eyewear, and relates more particularly to plano eyewear for use in safety and recreational applications and methods of designing and manufacturing the same.

DESCRIPTION OF THE BACKGROUND

Traditional plano (that is, non-corrective or zero power) eyewear is characterized by a plate or lens that offers protection for a user's eyes while providing a relatively unobstructed view of objects beyond the lens.

Traditional plano lenses have many disadvantages that create visual discomfort for the user in some situations and/or create safety issues when used as safety or impact resistance lenses.

Accordingly, a need or potential for benefit exists for a lens that overcomes the disadvantages of existing plano eyewear.

BRIEF DESCRIPTION OF THE DRAWINGS

To facilitate further description of the embodiments, the following drawings are provided in which:

FIG. 12 illustrates a lens with a cylindrical surface and an elliptical cylindrical surface, according to a fourth embodiment;

FIG. 13 illustrates a cross-sectional view of the lens of FIG. 12 along the line XIII-XIII of FIG. 12, according to the fourth embodiment;

FIG. 18 include a table illustrating various properties of lens of FIG. 1 and various prior art lenses.

Figure 1:
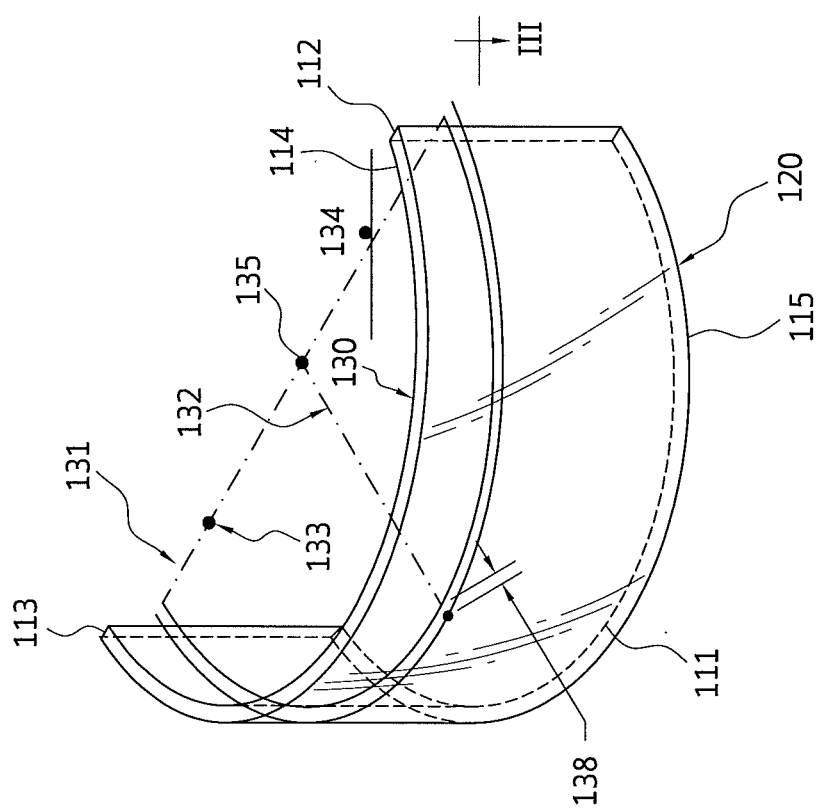
FIG. 1 illustrates a lens with a cylindrical surface and an elliptical cylinder surface, according to a first embodiment.

For simplicity and clarity of illustration, the drawing figures illustrate the general manner of construction, and descriptions and details of well-known features and techniques may be omitted to avoid unnecessarily obscuring the invention. Additionally, elements in the drawing figures are not necessarily drawn to scale. For example, the dimensions of some of the elements in the figures may be exaggerated relative to other elements to help improve understanding of embodiments of the present invention. The same reference numerals in different figures denote the same elements.

The terms "first," "second," "third," "fourth," and the like in the description and in the claims, if any, are used for distinguishing between similar elements and not necessarily for describing a particular sequential or chronological order. It is to be understood that the terms so used are interchangeable under appropriate circumstances such that the embodiments described herein are, for example, capable of operation in sequences other than those illustrated or otherwise described herein. Furthermore, the terms "include," and "have," and any variations thereof, are intended to cover a non-exclusive inclusion, such that a process, method, system, article, device, or apparatus that comprises a list of elements is not necessarily limited to those elements, but may include other elements not expressly listed or inherent to such process, method, system, article, device, or apparatus.

The terms "left," "right," "front," "back," "top," "bottom," "over," "under," and the like in the description and in the claims, if any, are used for descriptive purposes and not necessarily for describing permanent relative positions. It is to be understood that the terms so used are interchangeable under appropriate circumstances such that the embodiments of the invention described herein are, for example, capable of operation in other orientations than those illustrated or otherwise described herein.

The terms "couple," "coupled," "couples," "coupling," and the like should be broadly understood and refer to connecting two or more elements, mechanically and/or otherwise. The absence of the word "removably," "removable," and the like near the word "coupled," and the like does not mean that the coupling, etc. in question is or is not removable.

DETAILED DESCRIPTION OF EXAMPLES OF EMBODIMENTS

Some embodiments concern a lens for protection of one or more eyes of a user. The lens can include: a first surface; and a second surface spaced apart from the first surface such that the lens has a variable thickness between the first surface and the second surface. The first surface can include substantially an arc. The second surface can include a substantially elliptical curve and the lens can be a smooth, arcuate, substantially plano lens.

Another embodiment can concern eyewear for protection of the eyes of a user where the eyewear includes: a frame; and a unitary lens coupled to the frame, the unitary lens has a center, a first peripheral edge spaced apart from the center, a second peripheral edge spaced apart from the center and the first peripheral edge, the unitary lens has: a first surface extending from the first peripheral edge to the second peripheral edge; and a second surface spaced apart from the first surface and extending from the first peripheral edge to the second peripheral edge. When the eyewear is worn by the user, the first surface and the second surface of the unitary lens covers both of the eyes of the user. The first surface has at least one of a toroidal curvature, a cylindrical curvature, a spherical curvature, or a conical curvature. The second surface can include a substantially elliptical curvature. The unitary lens is a smooth, substantially plano lens. When the eyewear is worn by the user, an inner surface of the unitary lens is closer to the eyes of the user than an outer surface of the unitary lens. One of the first surface or the second surface is the inner surface of the unitary lens and one of the first surface or the second surface is the outer surface of the unitary lens.

A further embodiment can concern a method of designing eyewear. The eyewear can include a lens, where the lens has a first surface and a second surface spaced apart from the first surface, the lens further has a center and two peripheral ends, and the two peripheral ends are spaced apart from the center of the lens and each other. The method can include: defining two points of an arc on the first surface of the lens such that the first surface comprises at least one of a toroidal curvature, a spherical curvature, a cylindrical curvature, or a conical curvature; defining a center thickness of the lens where the center thickness is a first thickness of the lens at the center of the lens; defining a peripheral thickness of the lens where the peripheral thickness is a second thickness of the lens at the two peripheral ends of the lens; and creating the lens using the two points on the arc, the center thickness of the lens, and the peripheral thickness of the lens such that the second surface has a substantially elliptical curvature and such that the lens is smooth and provides at least one of: a horizontal prism of substantially zero; a power of substantially zero; or astigmatism of substantially zero.

Yet another embodiment can concern a method of manufacturing eyewear with a lens. The method can include: using at least one computer numerical control machine to create a first lens mold surface of a lens mold for a first surface of a lens wherein the first surface comprises at least one of a toroidal curvature, a spherical curvature, a cylindrical curvature, or a conical curvature; using the at least one computer numerical control machine to create a second lend mold surface for a second surface of the lens such that: (a) the second surface has a substantially elliptical curvature, (b) the lens has a first thickness at a center of the lens, (c) the lens has a second thickness at two peripheral edges of the lens, (d) the lens has a third thickness at a point between the center of the lens and each of the peripheral edges of the lens, and (e) the lens provides at least one of: a horizontal prism of substantially zero; a power of substantially zero; or astigmatism of substantially zero; and using the lens molds to create the lens of the eyewear. The first thickness is greater than or equal to the second thickness. The first thickness is greater than the third thickness. The second thickness is greater than the third thickness.

In some examples, the eyewear can be spectacles, goggles, face shields, respirator lenses, visors, helmets, and the like.

Figure 2:
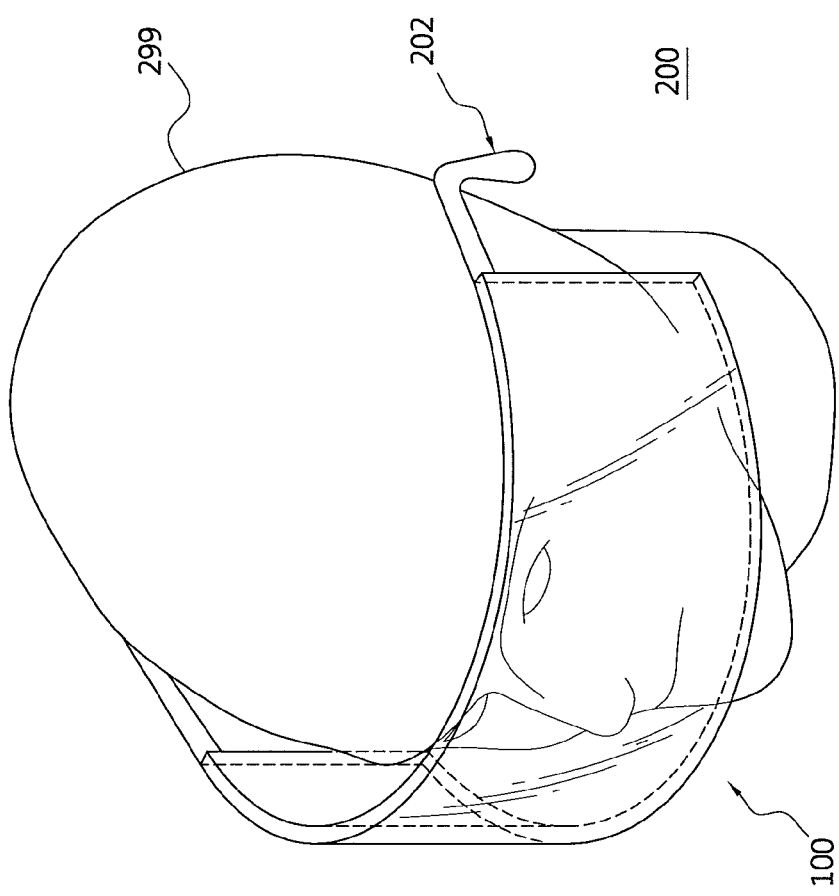
FIG. 2 illustrates eyewear with the lens of FIG. 1 being worn by a user, according to the first embodiment.
Figure 3:
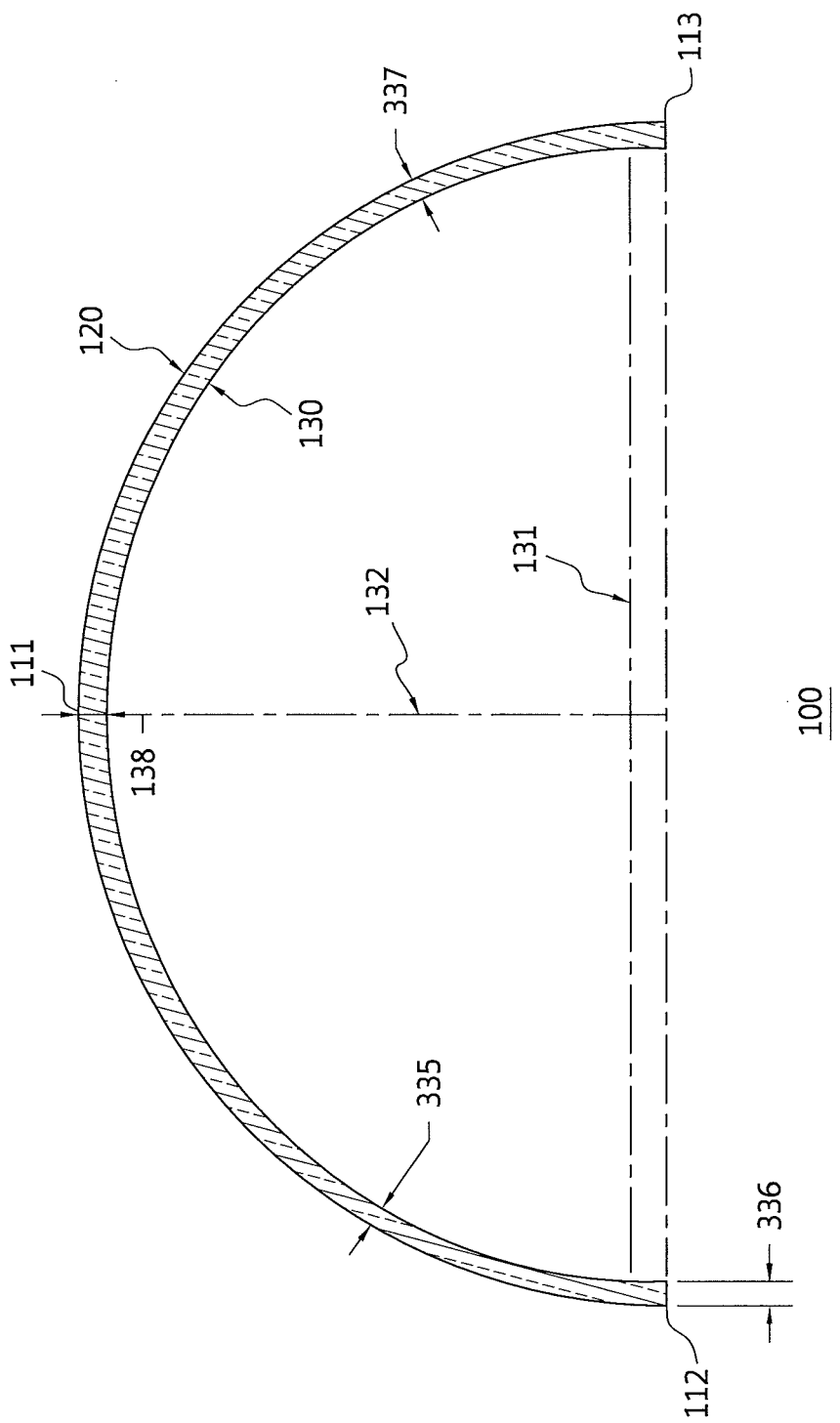
FIG. 3 illustrates a cross-sectional view of the lens of FIG. 1 along the line III-III (FIG. 1), according to the first embodiment.

Turning to the drawings, FIG. 1 illustrates a lens 100 with a cylindrical surface and an elliptical cylindrical surface, according to a first embodiment. FIG. 2 illustrates eyewear 200 with lens 100 being worn by a user 299, according to the first embodiment. FIG. 3 illustrates a cross-sectional view of lens 100 along the line III-III (FIG. 1), according to the first embodiment. Lens 100 is merely exemplary and is not limited to the embodiments presented herein. Lens 100 can be employed in many different embodiments or examples not specifically depicted or described herein.

Referring to FIGS. 1-3, in some examples, eyewear 200 can be used for the protection of the eyes of a user 299 (FIG. 2). Eyewear 200 can include: (a) a frame 202 configured to hold lens 100 over one or both of the eyes of user 299; and (b) a lens 100 coupled to frame 202. In some examples, the lens can be made from polyestic, polycarbonate, or blends of the two.

In various embodiments, lens 100 can include: (a) a center 111; (b) a first peripheral (i.e., lateral) edge 112 spaced apart from center 111; (c) a second peripheral (i.e., lateral) edge 113 spaced apart from center 111 and first peripheral edge 113; (d) an outer surface 120 extending from first peripheral edge 112 to second peripheral edge 113; (e) an inner surface 130 spaced apart from outer surface 120 and extending from first peripheral edge 112 to the second peripheral edge 113; (f) a top side 114 extending from first peripheral edge 112 to the second peripheral edge 113 and from outer surface 120 to inner surface 130; and (g) a bottom side 115 spaced apart from top side 114 and extending from first peripheral edge 112 to the second peripheral edge 113 and from outer surface 120 to inner surface 130. When eyewear 200 is worn by user 299, inner surface 130 can cover both of the eyes of user 299 and is closer to the eyes of user 299 than outer surface 120.

In the example shown in FIGS. 1-3, lens 100 is a unitary lens and a half face shield. In various embodiments, lens 100 can be a unitary face shield or a unitary visor. In other embodiments, the lens can be other types of eyewear including a goggle lens or a bubble-type lens configured to cover a single eye of the user.

In many examples, lens 100 can be a smooth, arcuate, substantially plano lens. As used herein, "substantially plano" is defined as being zero power or a small amount (e.g., +/−1/16th of a diopter or less), preferably of negative power. Furthermore, as used herein, "smooth" is defined as a curve with substantially zero change in curvature in the first and second order. That is, a smooth curve has no sudden changes of the rate of change of the curvature on the first and second order.

Use of a smooth curve on surfaces 120 and 130 provides an advantage over prior art lenses with irregular and/or unsmooth surfaces or blended surfaces. For example, some prior art lenses are designed using computer design software where the lens designer optimizes the optical properties of the lens at a predetermined number of point (e.g., 12, 16, 32, or 128 points on a lens). While lenses designed using this prior art method may have many useful optical properties, these lenses tend to have at least one irregular and unsmooth surface. In the embodiments described herein, the surfaces of the lens are smooth, which allows easy manufacturing of the lens. Lenses with irregular and/or unsmooth surface may have some similar optical properties as the embodiments described herein, but such irregularities will cause visual discomfort. Moreover, the irregular and/or unsmooth surfaces may be difficult or impossible to manufacture. In other prior art lenses, efforts are made to add blended surfaces outside the optical surface in order to maintain edge thickness rather than continuing to taper. Such transitions constitute local changes in curvature and power. These transitions are visible to wearers and can cause visual discomfort if they come into the field of view. The embodiments described herein bring a combination of desirable optical properties (described below) and relative easy manufacturing process (described below).

In many embodiments, outer surface 120 is substantially an arc. In the example shown in FIG. 1, outer surface 120 has a cylindrical curvature. As will be described later, in other examples, an outer surface of an embodiment can have at least one of a toroidal curvature, a spherical curvature, or a conical curvature.

A cylindrical curve or surface is a curve or surface where the points along the curve or the surface are a fixed distance from an axis of the cylinder. Outer surface 120 can be a section of a cylinder and focus the image passing through it onto a line parallel to the intersection of outer surface 120 and a plane tangent to it. In some embodiments, outer surface 120 can have a radius between 60 and 120 mm. For example, a radius of surface 120 can be 100 mm.

In many examples, inner surface 130 can have a substantially elliptical surface. An ellipse is a smooth closed curve, which is symmetric about its horizontal and vertical axes Inner surface 130 can be a portion of an ellipse with semi-major axis 131 and a semi-minor axis 132. Semi-major axis 131 and the semi-minor axis 132 are one-half of the major and minor axes, respectively. The radius of semi-major axis 131 is a. The foci 133 and 134 of an ellipse are two points on major axis 131 and are equidistant from center 135 of the ellipse.

The eccentricity, c, of the ellipse defines the degree of departure of the ellipse from a circular shape. It is a measure of the flatness of the ellipse. The distance from center 135 of the ellipse to each foci 133 and 134 is defined as f. The distance, f, can also be defined as half the distance between foci 133 and 134. The eccentricity is defined as $\epsilon = f/a$ For a circle, the foci converge so that f=0 and therefore $\epsilon$=0. For a line, the focal points are the end points of the "ellipse" so that a=f and therefore $\epsilon$=1. Both lines and circles are technically mathematical ellipses, but they do not confer the advantages of the embodiments described herein. Because some embodiments require a certain flatness of curvature, but not so flat as to describe a line, an ellipse, as used herein, is defined as an ellipse with eccentricity, $\epsilon$, between 0 and 1 non-inclusive, or $0 < \epsilon < 1$.

Thus, a radius of semi-minor axis 132 must be greater than zero, and must not equal a radius of the semi-major axis 131. In some embodiments, the eccentricity of inner surface 130 can be between 0.001 and 0.375. In other examples, the eccentricity of inner surface 130 can be between 0.001 and 0.250. In still further examples, the eccentricity of inner surface 130 can be between 0.001 and 0.125. For example, the eccentricity of inner surface 130 can be 0.187.

Furthermore, because a lens is a three-dimensional surface, not a two-dimensional surface, a "substantially elliptical curve" as used herein can include an elliptical surface, elliptical conic surface, elliptical toric surface, elliptical spheric surface, ellipsoidal surface, or aspherical surface with a SAG coefficient of greater than zero but not greater than 1% of the ellipse's average radius.

As illustrated in FIG. 3, in many embodiments, inner surface 130 is spaced apart from outer surface 120 such that lens 100 has a variable thickness between inner surface 130 and outer surface 120. Lens 100 can have: (a) a first thickness 138 at a center 111 of lens 100; (b) a second thickness 336 at outboard or lateral edge 112 or 113 of lens 100; (c) a third thickness 335 at a position between center 111 of lens 100 and lateral edge 112 of lens 100; and (d) a fourth thickness 337 at a position between center 111 of lens 100 and lateral edge 113 of lens 100. First thickness 138, second thickness 336, third thickness 335, and fourth thickness 337 are distances between outer surface 120 of lens 100 and inner surface 130 of lens 100.

In many embodiments, the thickest portion of lens 100 is at center 111 of lens 100, and the thinnest point of lens 100 is between center 111 of lens 100 and peripheral edges 112 and 113 of lens 100. That is, first thickness 134 can be greater than or equal to second thickness 336, third thickness 335, and fourth thickness 337. Furthermore, second thickness 336 can be greater than or equal to third thickness 335 and fourth thickness 337 at least when third thickness 335 and fourth thickness 337 are at their minimum, third thickness 335 and fourth thickness 337 are less than second thickness 336. In many examples, third thickness 335 and fourth thickness 337 are equal to each other at portions equidistant from center 111 (i.e., lens 100 is symmetric around semi-minor axis 132). The location of the thinnest point of lens 100 can vary based upon the radii of outer surface 120 and inner surface 130, and the eccentricity and/or the nominal peripheral edge thickness of lens 100.

In some examples, first thickness 138 is approximately two millimeters to approximately six millimeters; second thickness 336 is between 7/10ths to 10/10ths of first thickness 138; and third thickness 335 and fourth thickness 337 are between 5/10ths to 8/10ths of first thickness 138.

FIGS. 4-7 illustrate examples of lenses 400, 500, 6000, and 700, respectively, with varying thicknesses and varying deviations in thicknesses. All of exemplary lenses 400, 500, 600, and 700 have an outer radius of 87.5 millimeters for illustration purposes, but such lenses could have a radius of 100 millimeters or more.

Figure 4:
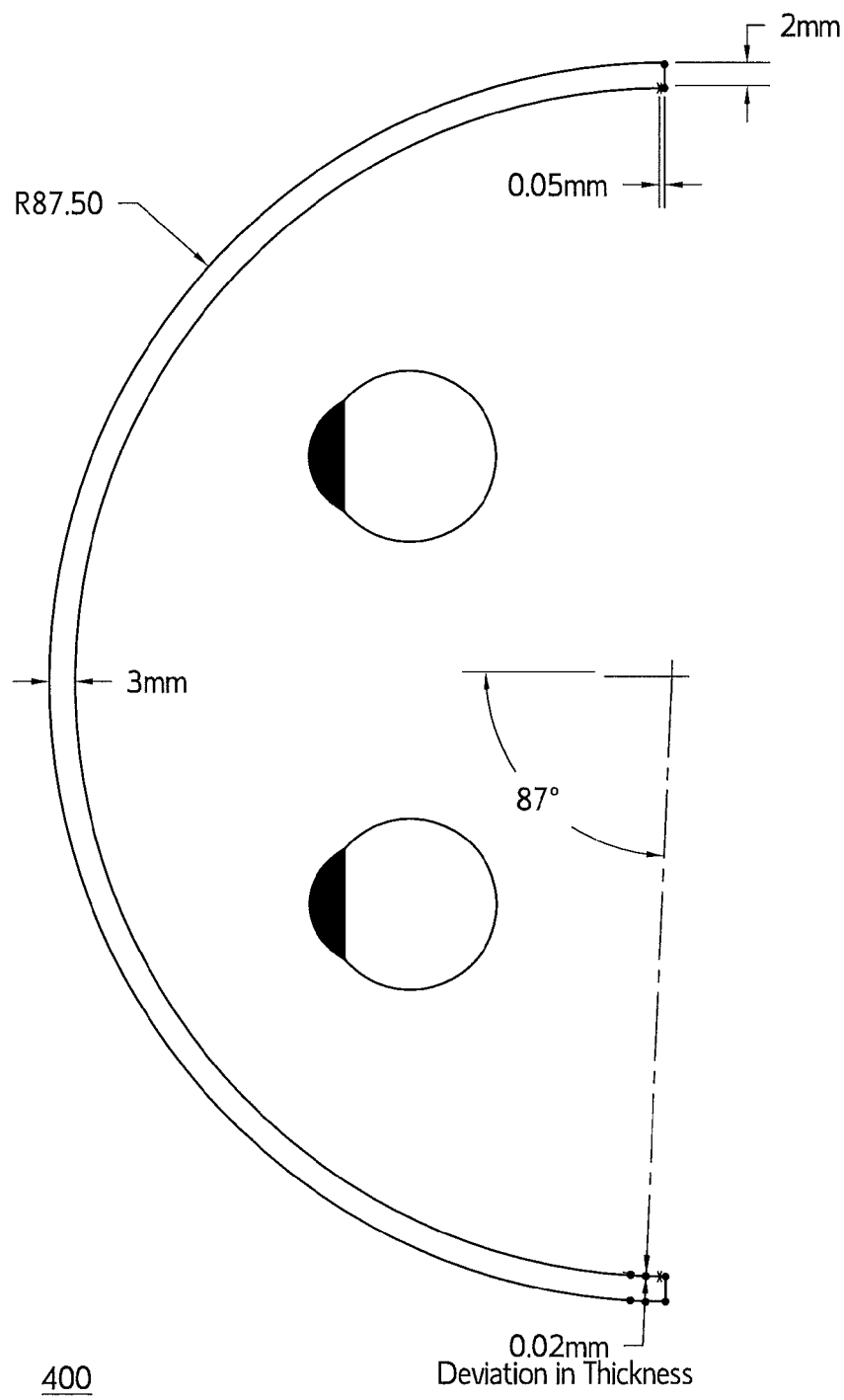
FIGS. 4-7 illustrate examples of lenses with varying thicknesses and varying deviations in thicknesses, according to the first embodiment.

In the example shown in FIG. 4, a thickness at the center of lens 400 is three millimeters, and the thickness of lens 400 at the peripheral edge of lens 400 is two millimeters. The maximum deviation of thickness of 0.02 millimeters occurs at an 88.6 degree angle with a center of the outer surface of lens 400.

Figure 5:
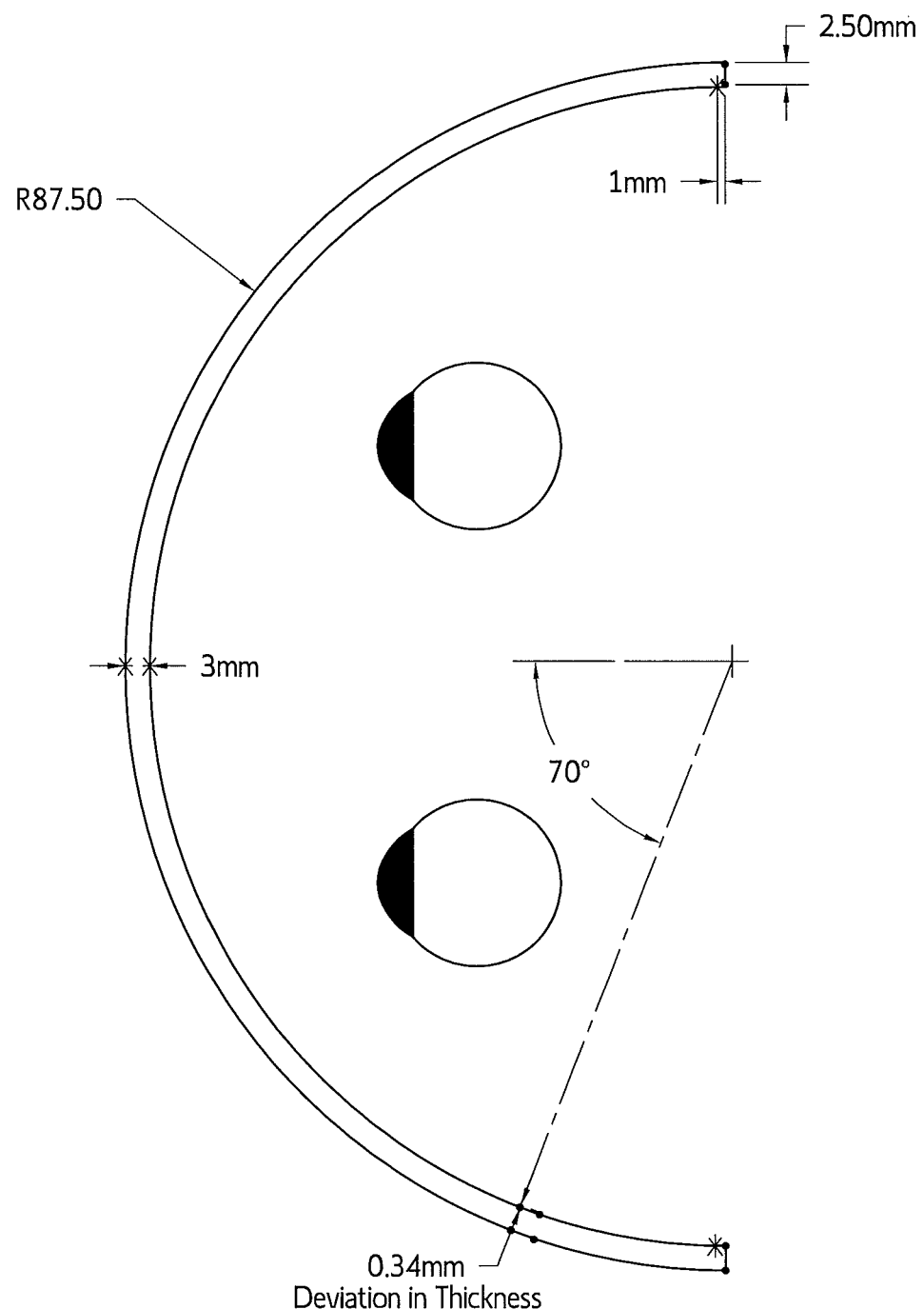

In the example shown in FIG. 5, a thickness at the center of lens 500 is three millimeters, and the thickness of lens 500 at the peripheral edge of lens 500 is 2.5 millimeters. The maximum deviation of thickness of 0.34 millimeters occurs at a 70.4 degree angle with a center of the outer surface of lens 500.

Figure 6:
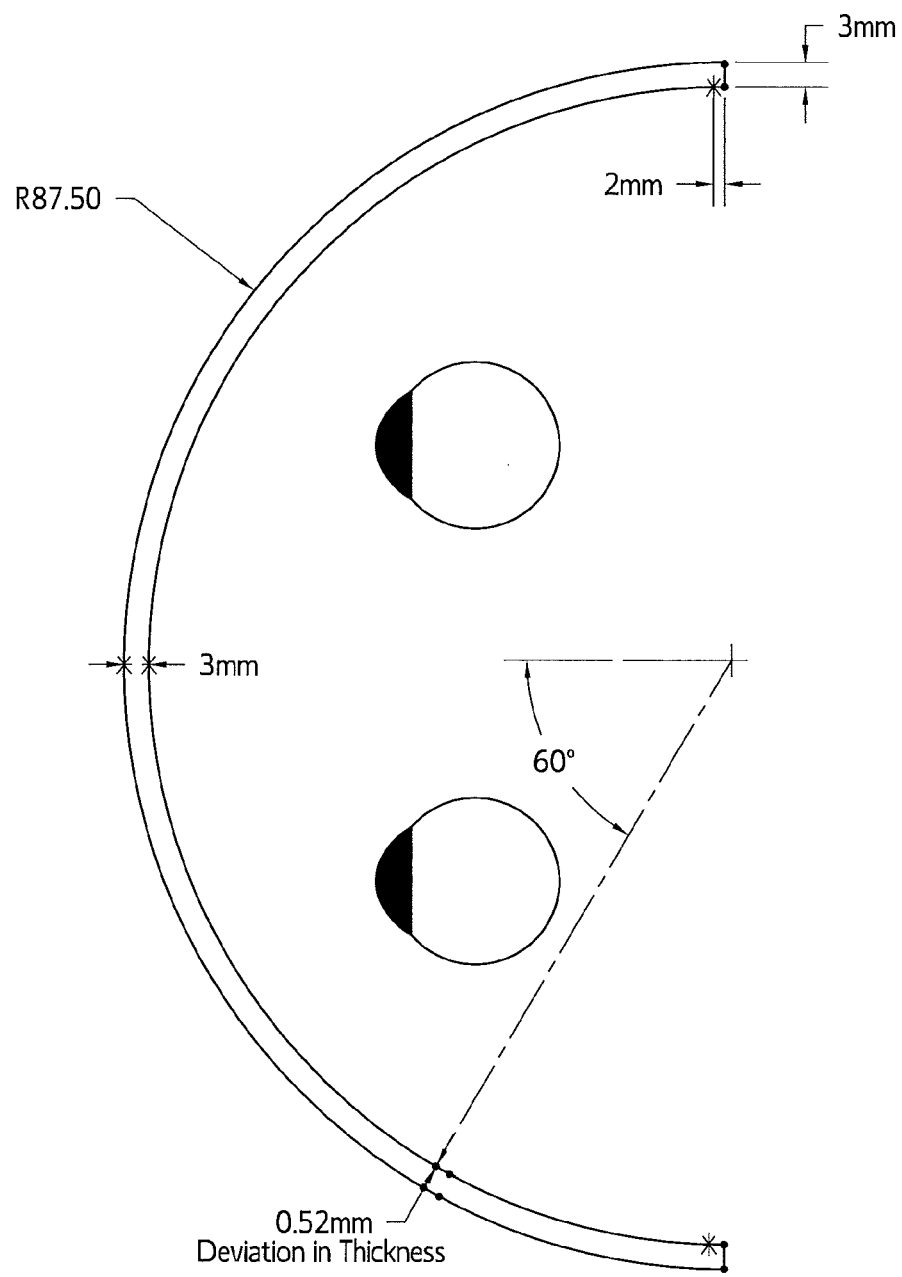

In the example shown in FIG. 6, a thickness at the center of lens 600 is three millimeters, and the thickness of lens 600 at the peripheral edge of lens 600 is three millimeters. The maximum deviation of thickness of 0.52 millimeters occurs at a 59.8 degree angle with a center of the outer surface of lens 600. In other examples, a thickness of the center of lens 400, 500, or 600 can be two millimeters. In the same or different example, a thickness of the peripheral edge of the lens 400, 500, or 600 can be equal to a thickness of the center of lens 400, 500, or 600, respectfully.

Figure 7:
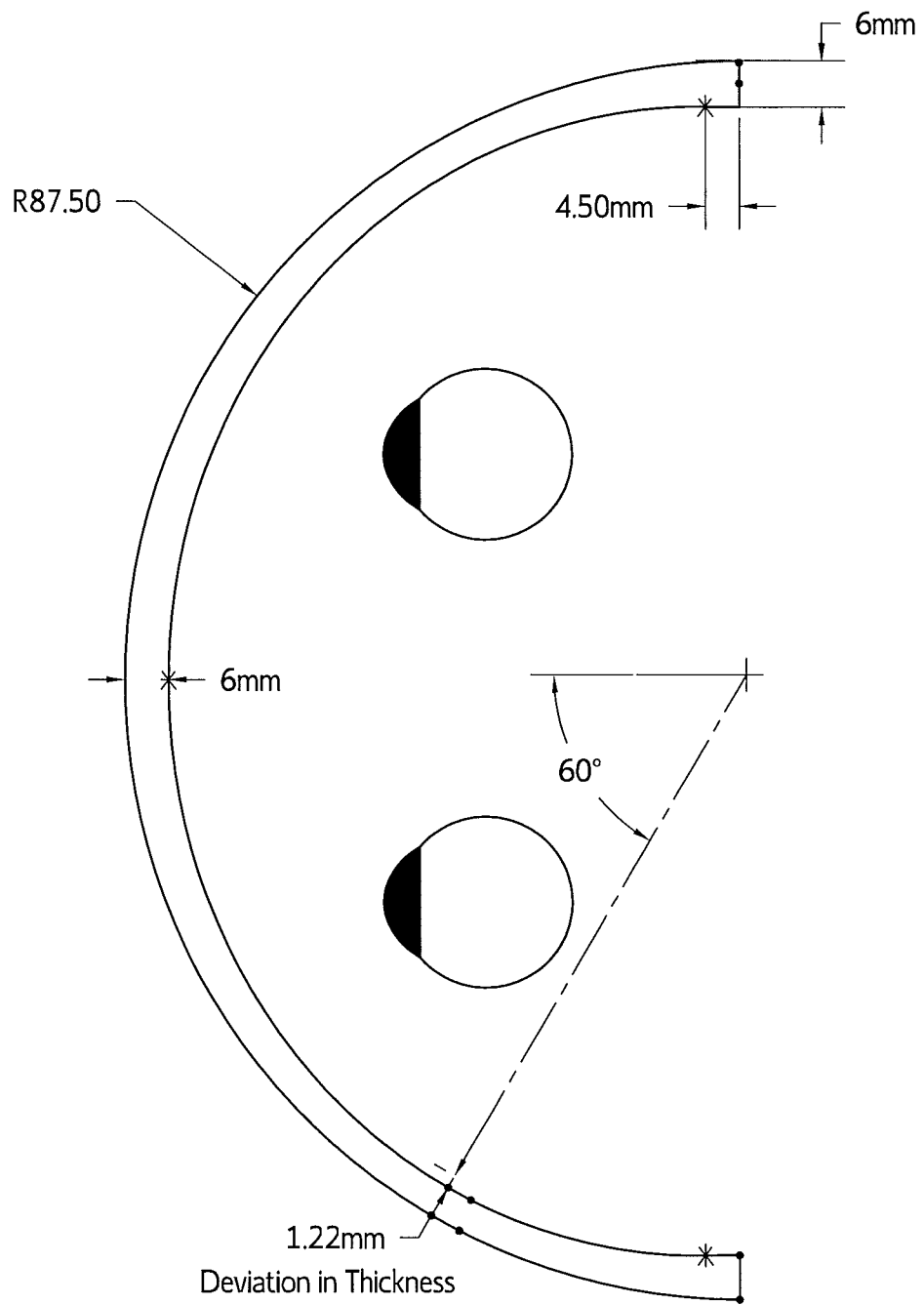

In the example shown in FIG. 7, a thickness at the center of lens 700 is six millimeters and the thickness of lens 700 at the peripheral edge of lens 700 is six millimeters. The maximum deviation of thickness of 1.22 millimeters occurs at a 59.5 degree angle with a center of the outer surface of lens 700.

Having a thicker peripheral edge can improve the impact and ballistic resistance of lens 100 (and the other lenses described herein). When a lens undergoes an impact, much of the force and pressure of the impact is placed on the peripheral edges of the lens. Accordingly, prior art lenses that taper from the center to the peripheral edges break or crack easier when an impact occurs. Lens 100 (and the other lenses described herein) improves the impact and ballistic resistance while avoiding the problems of using thicker lenses, unsmooth lenses, or lenses with a constant thickness.

In many examples, lens 100 (and the other lenses described herein) comply with an impact resistance requirement of at least one of:
(a) the ANSI/ISEA (American National Standard Institute) Z87.1-2010 standard;

(b) the CSA (Canadian Standards Association) Z94.3.1-09 standard
(c) the European EN 166 (2002) and EN 169 (2002) standards;
(d) the MIL-DTL-43511D (2006) standard;
(e) the U.S. military MIL-STD-662 (1997) standard;
(f) the U.S. military MIL-PRF-31013 (1996) standard;
(g) the NFPA (National Fire Protection Association) standard
(h) the Canadian CAN/CSA-Z262.2-M90 standard;
(i) the ASTM (American Society for Testing and Materials) F513-12;
(j) ASTM F1776-12;
(k) ASTM F803-11;
(l) ASTM F 2713-09;
(m) CSA Z262.2-09;
(n) Z94.3-07(R2012);
(o) CSA P400-M1982; and/or
(p) AS/NZ 4066.

Lens 100 (and lenses 400, 500, 600, and 700) can provide optical properties that are much improved over conventional prior art lenses. For example, lens 100 (i.e., a combination of outer surface 120 and inner surface 130) can provide a horizontal prism of substantially zero and a significantly reduced horizontal prism imbalance in the lateral gaze. As used herein, "a horizontal prism of substantially zero" means zero diopter or 0.125 diopters of base out prism or less. In the same or different example, lens 100 (and lenses 400, 500, 600, and/or 700) provides at least one of: a horizontal prism of substantially zero; a power of substantially zero; or astigmatism of substantially zero.

Moreover, lens 100 can provide a smooth transition from the forward to the lateral gaze in first and second orders and thus, provide visual comfort when compared to traditional prior art lenses. In addition, lens 100 provides reduced power, astigmatism, prism, and prism imbalance. In many examples, power, astigmatism, prism, and prism imbalance can be substantially zero. FIG. 18 include a table illustrating various properties of lens 100 and various prior art lenses.

In comparison with convention lenses where the thickness of the lens tapers from the center of the lens to the peripheral edge of the lens, prismatic distortion in the nasal eye can be quite problematic and transition from the forward to the lateral gaze is significant on the first and the second order. The effects of transition from the forward to the lateral gaze can cause visual discomfort, fatigue, nausea, and headaches when using prior art lenses. Moreover, any improvements in the forward gaze made by adjusting the physical properties of prior art lenses are often at the detriment of the lateral gaze, and these changes may cause significant visual discomfort. Lens 100 (and the other lenses) described herein decrease and/or eliminate these problems by providing a smooth transition from the forward to the lateral gaze in first and second orders.

While a prior art lens with a constant thickness is an improvement over prior art lenses with a taper, negative power, astigmatism, prism and prism imbalance are considerable and can make such lenses uncomfortable. As described above, lens 100 (and the other lenses) described herein decrease and/or eliminate these problems In the example shown in FIG. 1, inner surface 130 can have an elliptical curvature and outer surface 120 can have an arc-shape. In other examples, the inner surface of the lens can have an arc-shape and the outer surface of the lens can have elliptical curvature.

Figure 8:
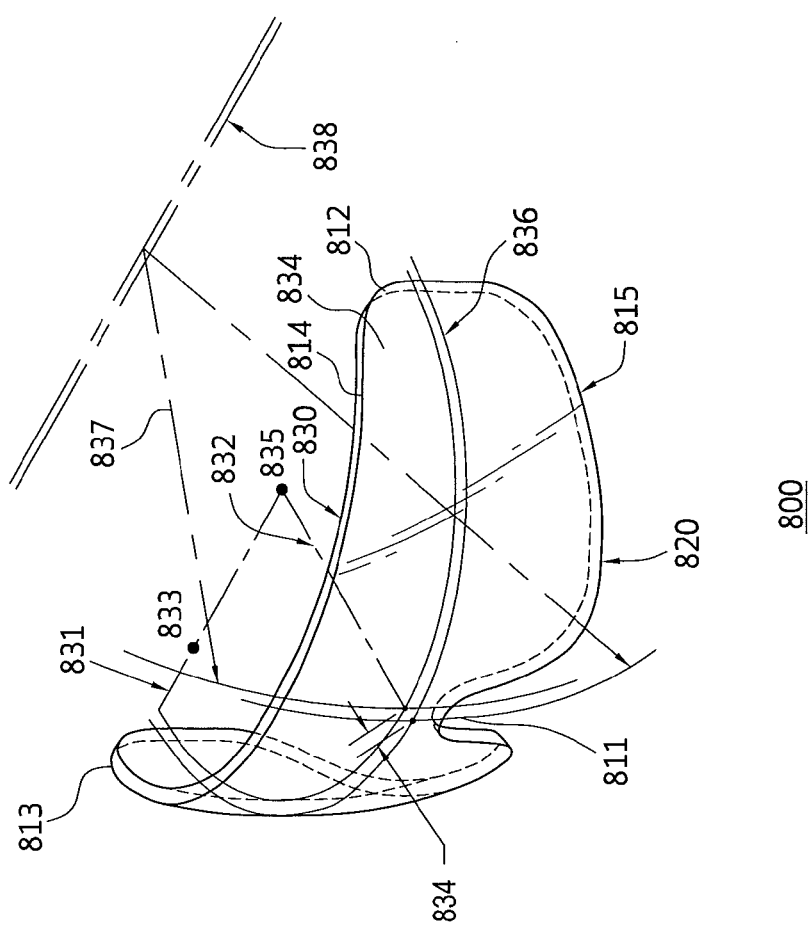
FIG. 8 illustrates a lens with a spherical or toric surface and an elliptical toric surface, according to a second embodiment.
Figure 9:
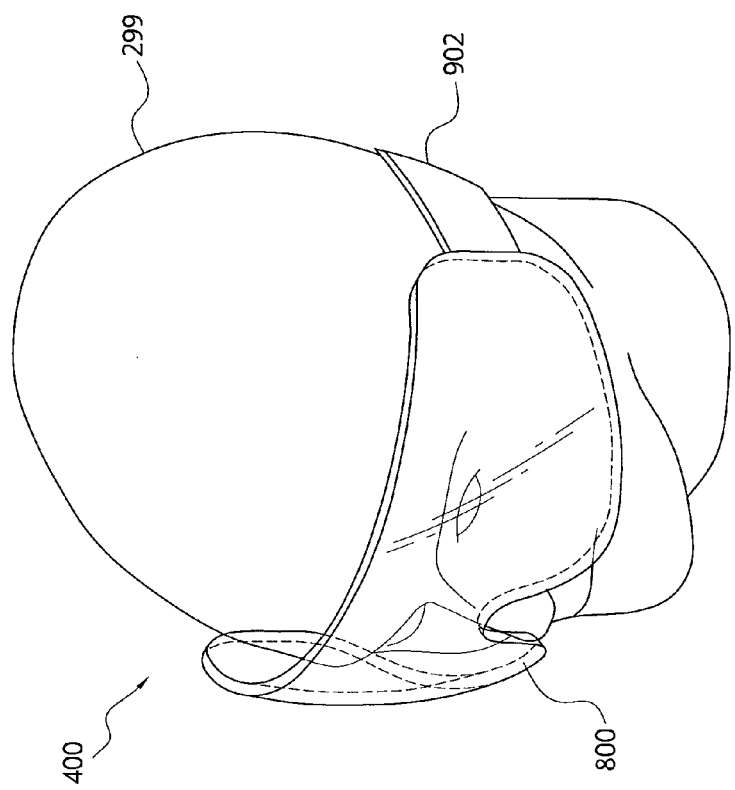
FIG. 9 illustrates eyewear with the lens of FIG. 8 being worn by a user, according to the second embodiment.

FIG. 8 illustrates a lens 800 with a spherical or toric surface and an elliptical toric surface, according to a second embodiment. FIG. 9 illustrates eyewear 900 with lens 800 being worn by user 299, according to the second embodiment. Lens 800 is merely exemplary and is not limited to the embodiments presented herein. Lens 800 can be employed in many different embodiments or examples not specifically depicted or described herein. In the example shown in FIGS. 8-9, eyewear 800 is goggles. In other examples, other types of eyewear can be created using lens 800.

Referring to FIGS. 8-9, in some examples, eyewear 900 (FIG. 9) can be used for the protection of the eyes of user 299 (FIG. 9). Eyewear 900 can include: (a) a frame 902 (FIG. 9) configured to hold the lens over one or both of the eyes of user 299; and (b) a lens 800 coupled to frame 902. In some example, lens 800 could be mounted under a visor or on a helmet.

In various embodiments, lens 800 can include: (a) a center 811; (b) a first peripheral (i.e., lateral) edge 812 spaced apart from center 811; (c) a second peripheral (i.e., lateral) edge 813 spaced apart from center 811 and first peripheral edge 813; (d) an outer surface 820 extending from first peripheral edge 812 to second peripheral edge 813; (e) an inner surface 830 spaced apart from outer surface 820 and extending from first peripheral edge 812 to the second peripheral edge 813; (f) a top side 814 extending from first peripheral edge 812 to the second peripheral edge 813 and from outer surface 820 to inner surface 830; and (g) a bottom side 815 spaced apart from top side 814 and extending from first peripheral edge 812 to the second peripheral edge 813 and from outer surface 820 to inner surface 830. When eyewear 900 is worn by user 299, inner surface 830 covers both of the eyes of user 299 and is closer to the eyes of user 299 than outer surface 820.

In many examples, inner surface 830 can have a substantially elliptical surface. In numerous examples, inner surface 830 can be identical or substantially similar to inner surface 130 of FIGS. 1-3. That is, inner surface 830 can be a portion of an ellipse with semi-major axis 831 and a semi-minor axis 832.

In the same or different embodiments, outer surface 820 can be a spherical or toroidal surface. Toroidal outer surface 820 can be the spatial surface resulting when a circle with radius 836 rotates around an axis 837 lying within the same plane as the circle, at a radius 838 from the circle's center. If radius 838 is greater than radius 836, a ring toroidal surface is produced. Lenses using ring torics usually have a horizontal axis of rotation, where lenses with horizontal curvature have elevated surfaces and lenses with vertical curvature are generally flatter than lenses with vertical curvature. If radius 838 is equal to radius 836, a sphere can be obtained. Radius 838 can be less than radius 836 results in a spindle toroidal surface, where the surface contracts to a point like a football. Generally, lenses using spindle torics have the axis of rotation vertical, horizontal curvature is elevated, and vertical curvature is generally flatter. A good example is a motorcycle or snowmobile helmet lens.

In some embodiments, radius 836 can be between 80 mm and 100 mm so as to fit the face. In the same or different embodiments, radius 838 can be between 120 and 500 mm depending on the desired shape. In one example, radius 836 can be approximately 100 mm and radius 838 can be approximately 200 mm.

In addition, similar to lens 100 (FIG. 1), the thickest point of lens 800 is at center 811 of lens 800, and the thinnest point of lens 800 is between center 811 of lens 800 and peripheral edges 812 and 813 of lens 800. The location of the thinnest point of lens 100 can vary based upon the eccentricity and radius of inner surface 830, radii 836 and 838 of outer surface 820, and/or the nominal peripheral edge thickness of lens 800.

Lens 800 can provide optical properties that are much improved over conventional prior art lenses. For example, lens 800 can provide a horizontal prism of substantially zero and a significantly reduced horizontal prism imbalance in lateral gaze. Moreover, lens 800 can provide a smooth transition from the forward to the lateral gaze in first and second order and thus, provide improved visual comfort when compared to traditional prior art lenses. In addition, lens 800 provides reduced power, astigmatism, prism, and prism imbalance. In many examples, power, astigmatism, prism, and prism imbalance can be substantially zero.

Figure 10:
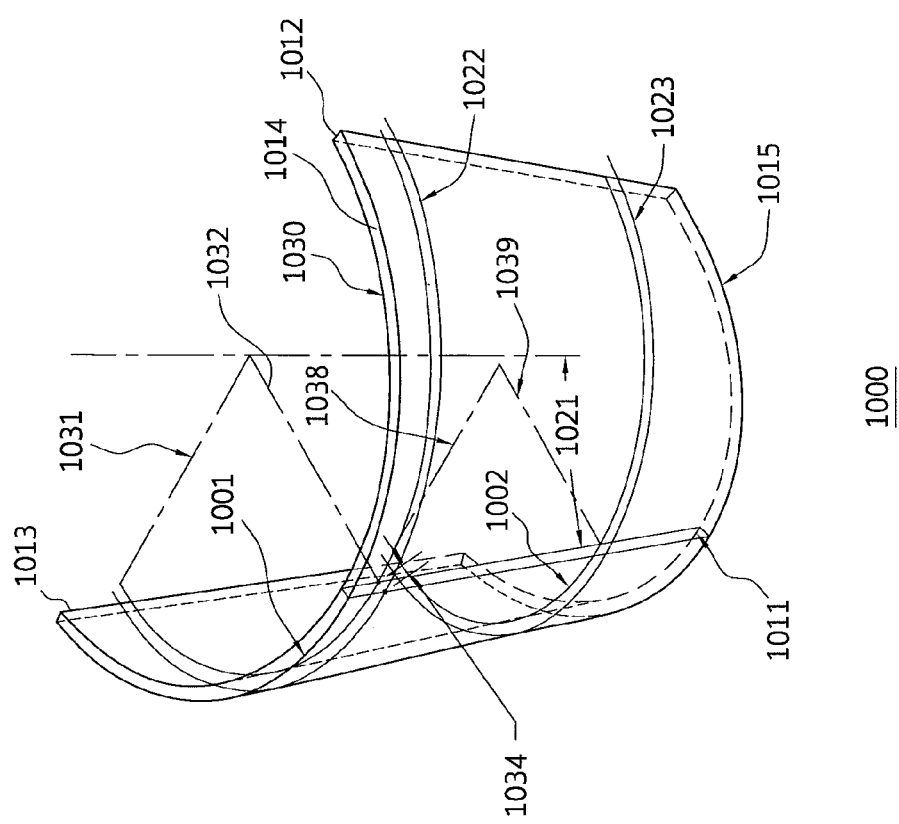
FIG. 10 illustrates a lens with a conical surface and an elliptical conical surface, according to a third embodiment.
Figure 11:
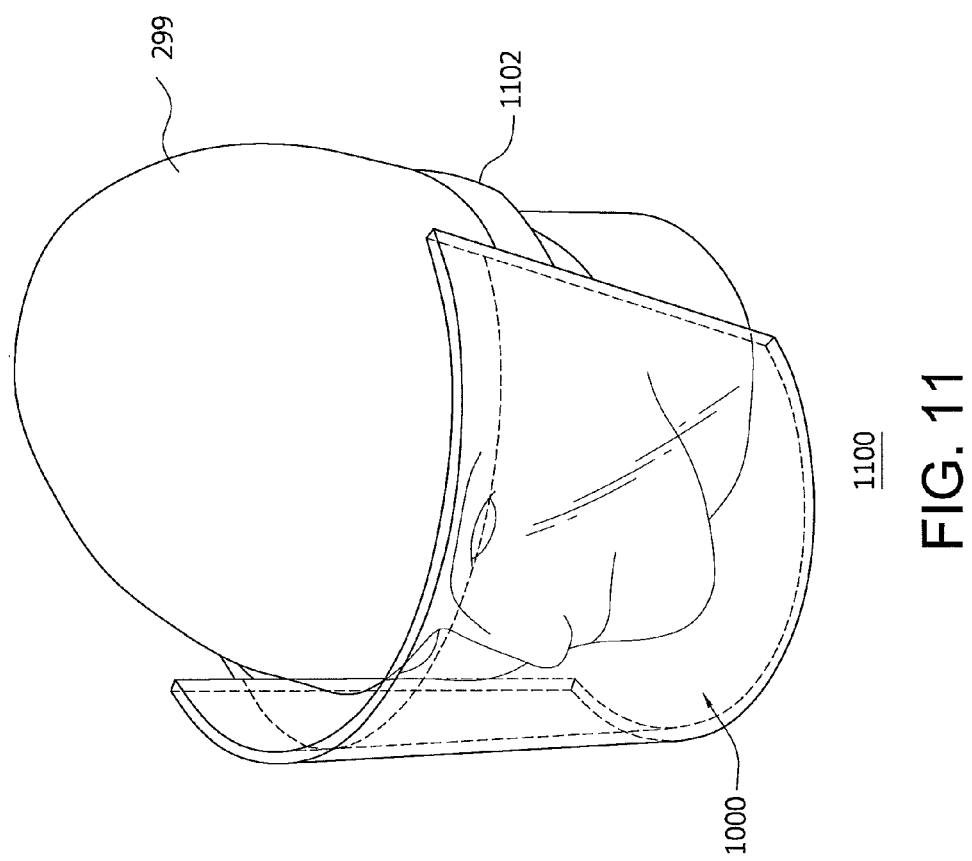
FIG. 11 illustrates eyewear with the lens of FIG. 10 being worn by a user, according to the third embodiment.

FIG. 10 illustrates a lens 1000 with a conical surface and a conical elliptical surface, according to a third embodiment. FIG. 11 illustrates eyewear 1100 with lens 1000 being worn by user 299, according to the third embodiment. Lens 1000 is merely exemplary and is not limited to the embodiments presented herein. Lens 1000 can be employed in many different embodiments or examples not specifically depicted or described herein. In the example shown in FIG. 11, eyewear 1100 is a full face shield. In other examples, other types of eyewear can be created using lens 1000.

Referring to FIGS. 10-11, in some examples, eyewear 1100 (FIG. 11) can be used for the protection of the eyes of user 299. Eyewear 1100 can include: (a) a frame 1102 (FIG. 1) configured to hold the lens over both of the eyes of user 299; and (b) a lens 1000 coupled to frame 1102. In some examples, lens 1000 can be mounted to a helmet, a visor, a headband, or safety eyewear frame.

In various embodiments, lens 1000 can include: (a) a center 1011; (b) a first peripheral (i.e., lateral) edge 1012 spaced apart from center 1011; (c) a second peripheral (i.e., lateral) edge 1013 spaced apart from center 1011 and first peripheral edge 1013; (d) an outer surface 1020 extending from first peripheral edge 1012 to second peripheral edge 1013; (e) an inner surface 1030 spaced apart from outer surface 1020 and extending from first peripheral edge 1012 to the second peripheral edge 1013; (f) a top side 1014 extending from first peripheral edge 1012 to the second peripheral edge 1013 and from outer surface 1020 to inner surface 1030; and (g) a bottom side 1015 spaced apart from top side 1014 and extending from first peripheral edge 1012 to the second peripheral edge 1013 and from outer surface 1020 to inner surface 1030. When eyewear 900 is worn by user 299, inner surface 1030 covers both of the eyes of user 299 and is closer to the eyes of user 299 than outer surface 1020.

Inner surface 1030 can have a substantially elliptical surface. In many embodiments, inner surface 1030 can have at least two different elliptical curvatures 1001 and 1002. In this example, inner surface 1030 has a first portion with elliptical curvature 1001 and a second portion with elliptical curvature 1002. Inner surface 1030 can be shaped such that the transition from elliptical curvature 1001 to elliptical curvature 1002 can be smooth and gradual.

Elliptical curvature 1001 can have a semi-major axis 1031 and a semi-minor axis 1032. Elliptical curvature 1002 can have a semi-major axis 1038 and a semi-minor axis 1039.

In some embodiments, the eccentricity of elliptical curvature 1001 can be between 0.001 and 0.375. In other examples, the eccentricity of elliptical curvature 1001 can be between 0.001 and 0.250. In still further examples, the eccentricity of elliptical curvature 1001 can be between 0.001 and 0.125. For example, the eccentricity of elliptical curvature 1001 can be 0.187.

In the same or different embodiments, the eccentricity of elliptical curvature 1002 can be between 0.001 and 0.375. In other examples, the eccentricity of elliptical curvature 1002 can be between 0.001 and 0.250. In still further examples, the eccentricity of elliptical curvature 1002 can be between 0.001 and 0.125. For example, the eccentricity of inner surface 1030 can be 0.187. In some examples, the eccentricity of curve 1002 may be slightly higher than curve 1001 due to the higher curvature and power issues. This issue can be corrected with more taper.

Two elliptical curvatures on inner surface 1030 are used because, as will be described below, outer surface 1020 is a conical surface (i.e., the curvature of the lens 1000 from bottom side 1015 to top surface 1014 changes) and thus, in some embodiments, requires the curvature of inner surface 1030 to change as the radius of outer surface 1020 changes when you hold the vertical thickness of lens 1000 constant.

Outer surface 1020 can be a conical surface. In general, in geometry, a cone is the unbounded surface formed by the union of all the straight lines that pass through a fixed point—the apex or vertex—and any point of some fixed space curve. In general, a cone comprises two congruent unbounded halves joined by the apex. As shown in FIGS. 10-11, outer surface 820 can comprise a conical surface (e.g., a curve obtained as the intersection of a cone with a plane).

In some examples, outer surface 1020 can have: (a) a first radius 1022; (b) a second radius 1023; and (c) an angle 1021 between 5 and 25 degrees In some embodiments, radius 1022 can be between 85 mm and 110 mm. In the same or different embodiments, radius 1022 can be between 100 mm and 125 mm. In one example, radius 1022 can be approximately 100 mm.

Similarly, radius 1023 can be between 40 mm and 60 mm. In the same or different embodiments, radius 1023 can be between 50 mm and 90 mm. In one example, radius 1023 can be approximately 50 mm.

Angle 1021 can be between 10 degrees and 20 degrees. In one example, angle 1021 can be between 5 and 25 degrees.

Also, similar to lens 100 (FIG. 1) and lens 800 (FIG. 8), the thickest point of lens 1000 is at center 1011 of lens 1000 and the thinnest point of lens 1000 is between center 1011 of lens 1000 and peripheral edges 1012 and 1013 of lens 1000. The location of the thinnest point of lens 1000 can vary based upon radii of surfaces 1020 and 1030, angle 1021, and/or the nominal peripheral edge thickness of lens 1000.

Lens 1000 can provide optical properties that are much improved over conventional prior art lenses. For example, lens 1000 can provide a horizontal prism of substantially zero and a significantly reduced horizontal prism imbalance in lateral gaze. Moreover, lens 1000 can provide a smooth transition from the forward to the lateral gaze in first and second order and thus, provide improved visual comfort when compared to traditional prior art lenses. In addition, lens 1000 provides reduced power, astigmatism, prism, and prism imbalance. In many examples, power, astigmatism, prism, and prism imbalance can be substantially zero.

Referring to another embodiment, FIG. 12 illustrates a lens 1200 with a cylindrical surface and an elliptical surface, according to a fourth embodiment. FIG. 13 illustrates a cross-sectional view of lens 1200 along the line XIII-XIII of FIG. 12, according to the fourth embodiment. Lens 1200 is merely exemplary and is not limited to the embodiments presented herein. Lens 1200 can be employed in many different embodiments or examples not specifically depicted or described herein.

Referring to FIGS. 11-12, in some examples, eyewear can be used for protection of the eyes of a user 299 (FIG. 2). Eyewear can include: (a) a frame 202 (FIG. 2) configured to hold lens 1200 over one or both of the eyes of user 299; and (b) a lens 1200 coupled to frame 202.

In various embodiments, lens 1200 can include: (a) a center 1311; (b) a first peripheral (i.e., lateral) edge 1212 spaced apart from center 1211; (c) a second peripheral (i.e., lateral) edge 1213 spaced apart from center 1311 and first peripheral edge 1213; (d) an outer surface 1220 extending from first peripheral edge 1212 to second peripheral edge 1213; (e) an inner surface 1230 spaced apart from outer surface 1220 and extending from first peripheral edge 1212 to the second peripheral edge 1213; (f) a top side 1214 extending from first peripheral edge 1212 to the second peripheral edge 1213 and from outer surface 1220 to inner surface 1230; and (g) a bottom side 1215 spaced apart from top side 1214 and extending from first peripheral edge 1212 to the second peripheral edge 1213 and from outer surface 1220 to inner surface 1230.

Lens 1200 can be similar to lens 100 (FIG. 1), except that inner surface 1230 has an arc and outer surface 1220 is a substantially elliptical surface.

In the example shown in FIGS. 12-13, inner surface 1230 is a cylindrical surface. In other examples, inner surface 1230 can have at least one of a toroidal curvature, a spherical curvature, or a conical curvature. In some embodiments, inner surface 1230 can have a radius 1229 between 75 mm and 120 mm. For example, a radius 1229 of inner surface 1230 can be 87.5 mm.

In some examples, the eccentricity can be between 0.001 and 0.375. In other examples, the eccentricity of elliptical curvature can be between 0.001 and 0.250. In still further examples, the eccentricity of elliptical curvature 1002 can be between 0.001 and 0.125. For example, the eccentricity of outer surface 1220 can be 0.187.

In the same or different examples, the ratio of minor/major axis of elliptical curvature can be between 99.99% and 93%. In other examples, ratio of minor/major axis of elliptical curvature can be between 99.99% and 97%. In still further examples, the eccentricity of elliptical curvature 1002 can be between 99.99% and 99.4%. For example, the ratio of minor/major axis of elliptical curvature of outer surface can be 98.25%.

In some embodiments, the eccentricity of inner surface 130 can be between 0.001 and 0.375. In other examples, the eccentricity of inner surface 130 can be between 0.001 and 0.250. In still further examples, the eccentricity of inner surface 130 can be between 0.001 and 0.125. For example, the eccentricity of inner surface 130 can be 0.187.

Also, similar to lens 100 (FIG. 1), lens 800 (FIG. 8), and lens 1000 (FIG. 10), the thickest point of lens 1200 is at center 1311 of lens 1200 and the thinnest point of lens 1200 is between center 1311 of lens 1200 and peripheral edges 1212 and 1213 of lens 1200. The location of the thinnest point of lens 1200 can vary based upon radii of surfaces 1020 and 1030, the eccentricity of inner surface 130, and/or the nominal peripheral edge thickness of lens 1000.

Lens 1200 can provide optical properties that are much improved over conventional prior art lenses. For example, lens 1200 can provide a horizontal prism of substantially zero and a significantly reduced horizontal prism imbalance in lateral gaze. Moreover, lens 1200 can provide a smooth transition from the forward to the lateral gaze in first and second order and thus, provide improved visual comfort when compared to traditional prior art lenses. In addition, lens 1200 provides reduced power, astigmatism, prism, and prism imbalance. In many examples, power, astigmatism, prism, and prism imbalance can be substantially zero.

Figure 17:
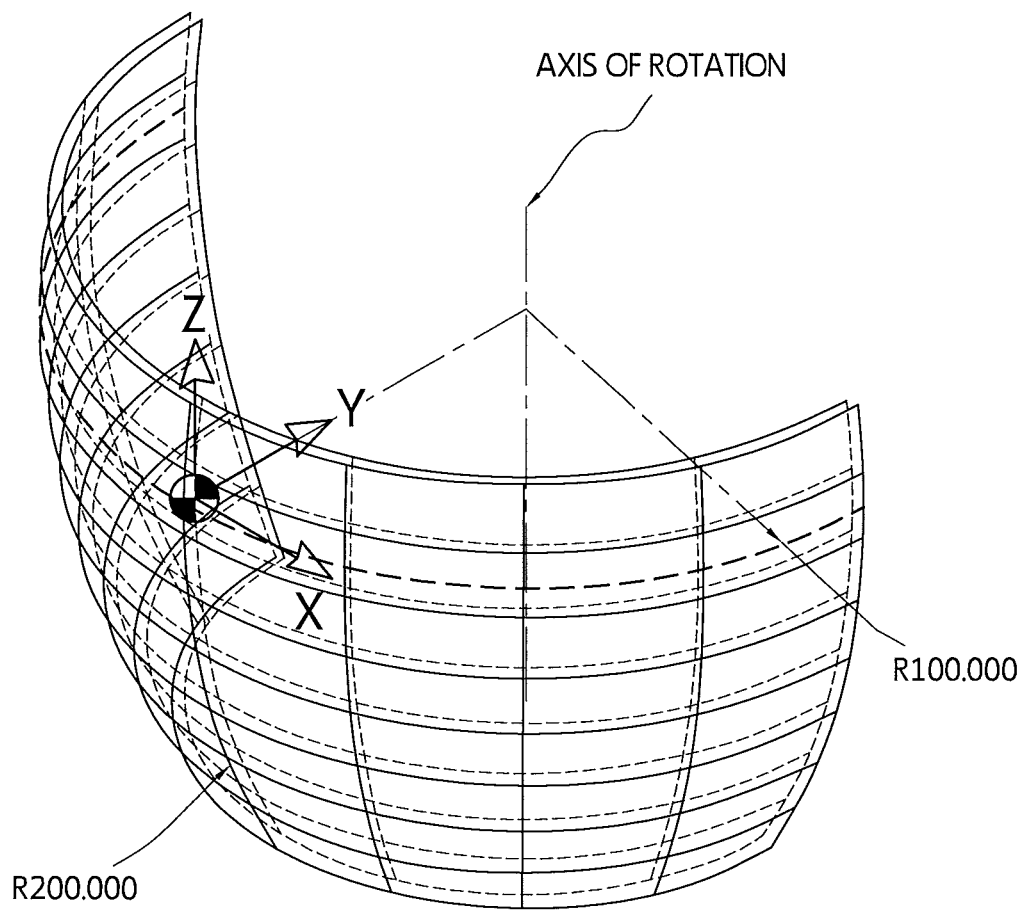
FIG. 17 illustrates an example of a transformation, according to an embodiment.

In addition to the examples described above in relation to FIGS. 1-13, many other possible geometries exist. For example, one surface of the lens can have a spindle toric surface (i.e., a surface created by an arc rotated around a short axis that yields a football-shaped surface) or in another example, a conical toric curvature (i.e., a horn-shaped surface created by rotating a circle about an axis while reducing its size in a linear fashion as it rotates, similar to a cone but around an arc rather than a straight line). Such surfaces can also be elliptically corrected by applying mathematical corrections to X, Y and Z coordinates (i.e., scaling 3D coordinates with specific factors in each direction). This method for correction can be applied to any surface that needs to be corrected elliptically. In this example, the origin of the coordinate system from which the scaling will originate is located on the optical origin of the inner surface to be corrected. In order to introduce elliptical correction in a horizontal plane to correct for optical issues emanating from interpupillary distance (i.e., in the Y direction), specific scaling factors can be applied to the X, Y and Z axes in order to introduce elliptical correction only in the Y direction, or in any other direction or combination thereof. FIG. 17 illustrates an example 1700 of this type of transformation, according to an embodiment.

Figure 14:
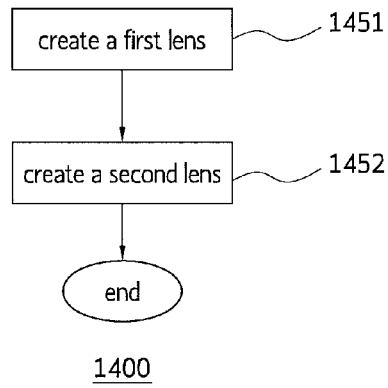
FIG. 14 illustrates a flow chart for an embodiment of a method of designing eyewear.

FIG. 14 illustrates a flow chart for an embodiment of a method 1400 of designing eyewear or a lens with an elliptical correction. Method 1400 is merely exemplary and is not limited to the embodiments presented herein. Method 1400 can be employed in many different embodiments or examples not specifically depicted or described herein. In some embodiments, the activities, the procedures, and/or the processes of method 1400 can be performed in the order presented. In other embodiments, the activities, the procedures, and/or the processes of method 1400 can be performed in any other suitable order. In still other embodiments, one or more of the activities, the procedures, and/or the processes in method 1400 can be combined or skipped.

Figure 15:
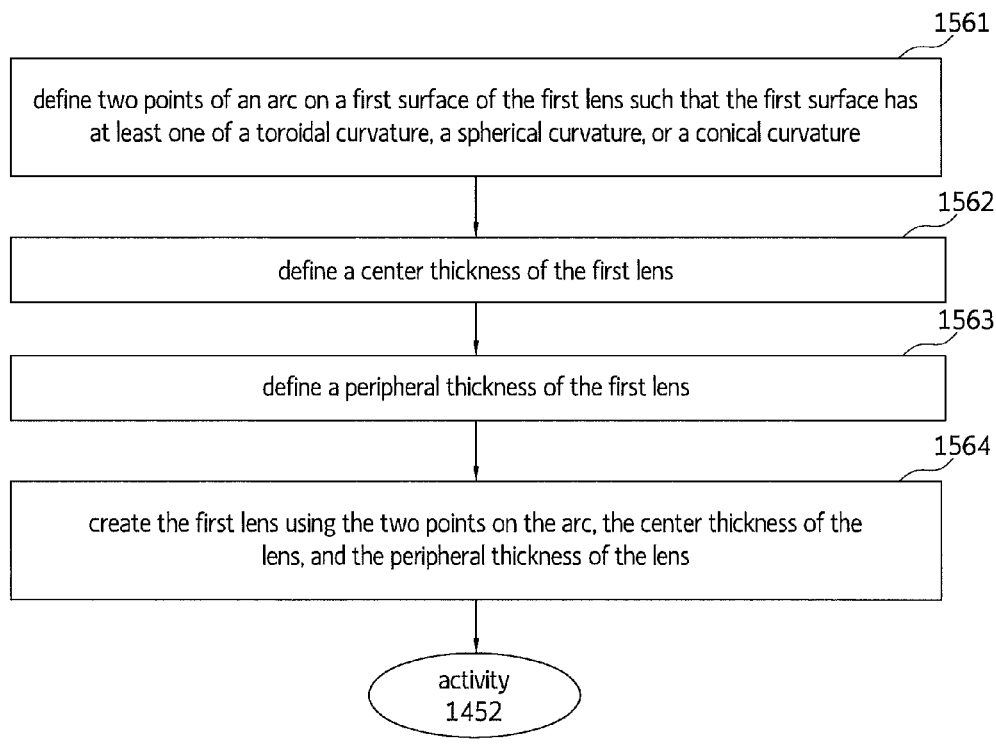
FIG. 15 illustrates a flow chart for an exemplary embodiment of an activity of creating a lens of the eyewear of FIG. 14.

Referring to FIG. 14, method 1400 includes an activity 1451 of creating a first lens. As an example, the first lens can be similar or identical to lenses 100, 400, 500, 600, 700, 800, 1000, or 1200 of FIGS. 1, 4, 5, 6, 7, 8, 10, and 12, respectively. FIG. 15 illustrates a flow chart for an exemplary embodiment of activity 1451 of creating the first lens.

Referring to FIG. 15, activity 1451 includes a procedure 1561 of defining two points of an arc on a first surface of the first lens such that the first surface has at least one of a toroidal curvature, a spherical curvature, or a conical curvature. In some examples, the two points of the arc can be defined to create a surface identical or similar to surface 120, 820, 1020, or 1230 of FIGS. 1, 8, 10, and 12, respectively. In some examples, this procedure can be performed using a computer aided design (CAD) software program or another software program running on a computer.

For example, the points on the arc can be chosen based on several different factors including: the fit with face, the visor or the helmet, minimal distances required for ventilation, respirators, displacement of lens during impact, prescription lenses, and other non-optical requirements.

Activity 1451 in FIG. 15 continues with a procedure 1562 of defining a center thickness of the first lens. The center thickness is a thickness of the first lens between the outer surface of the first lens and the inner surface of the first lens. In some examples, the center thickness of the lens can be approximately two millimeters to approximately six millimeters. In some examples, this procedure can be performed using a CAD program or another software program.

The center thickness of the lens can be chosen based on several different factors including: minimal thickness for impact protection, maximum weight of lens, and maximum and minimum thickness for molding of the lens Subsequently, activity 1451 of FIG. 15 includes a procedure 1563 of defining a peripheral thickness of the first lens. The peripheral thickness is a thickness of the lens at the two peripheral ends of the lens. In many examples, the thickness of the lens is the same at each of the two peripheral edges of the first lens. In some examples, the peripheral thickness of the lens can be between ⅜oths to ¹⁰⁄₁₀ths of the center thickness. In some examples, this procedure can be performed using a CAD program or another software program.

For example, the peripheral thickness of the lens can be chosen based on several different factors including: minimal thickness for impact protection, weight of lens, and/or the minimum thickness for molding of the lens.

Next, activity 1451 of FIG. 15 includes a procedure 1564 of creating the first lens using the two points on the arc, the center thickness of the lens, and the peripheral thickness of the lens. In some examples, the first lens is created such that the second surface has a substantially elliptical curvature and such that the lens is smooth and provides a horizontal prism of substantially zero. In many examples, the first lens is a smooth, substantially plano, unitary lens.

In some examples, the properties of the lens can be modified to improve the optical properties of the lens. For example, the proportions of the horizontal ellipse can be adjusted. In some examples, these proportions are adjusted to improve the optical qualities in the forward gaze. The parameters optimized can include horizontal prism in front of the eye. In other examples, the horizontal power can also be optimized. If the proportions of the ellipse that provide the desired optical properties offer an acceptable minimum thickness, the next adjustment can be to adjust oblique viewing optical properties based upon potential usage of the lens. If the proportions of the ellipse that provide the desired optical properties offer an acceptable minimum thickness, the center thickness and/or the peripheral thickness of the first lens can be adjusted.

For example, oblique viewing optical properties can be adjusted based upon potential usage of the lens. With the elliptical correction, the progression towards the lateral gaze is generally always improved. However, the center and edge thickness parameters can be altered to determine which combination provides the best combination of thickness (center and/or peripheral) and overall optical properties. In some examples, forward gaze can be more important than lateral gaze and the thickness can be adjusted to improve forward gaze. In other examples, lateral gaze can be more important than forward gaze and the thickness can be adjusted to improve lateral gaze.

In the same or different example, the properties of the lens can be modified to provide vertical correction. In some examples, an elliptical correction can be used if one of the surfaces of the lens has an ellipsoidal shape. In this example, the optical properties when gazing upwards and downwards are studied and adjustments are made to the surface accordingly. In many embodiments, the purpose of the adjustments is to balance optical properties in the vertical plane with the horizontal plane so as to reduce astigmatism to low or zero levels.

In some examples, this procedure can be performed using a CAD program or another software program. In other examples, a first portion of this procedure can be performed using a CAD program or another software program, and another portion of this procedure can be performed using an CNC machine used to create molds for optical lenses.

After procedure 1564, activity 1451 is complete.

Referring again to FIG. 14, method 1400 in FIG. 14 continues with an activity 1452 of creating a second lens. In some examples, where the eyewear is eyewear with two lenses (e.g., eyewear with double bubble lens), the second lens can be similar or identical to the first lens and activity 1452 can be similar or identical to activity 1451.

In one example, the first lens is a right lens of the eyewear and the second lens is a left lens of the eyewear. In some examples, the arcs of a first surface and the curvature of the second surface of the first lens and the second lens can be identical to each other. Similarly, the center thickness of the first lens and the second center thickness can be identical to each other. In the same or different example, the peripheral thickness of the first lens and the peripheral thickness of the second lens can be identical to each other.

In examples where the eyewear has only one lens (e.g., a face shield), activity 1452 can be skipped or omitted. After activity 1452, method 1400 is complete.

Figure 16:
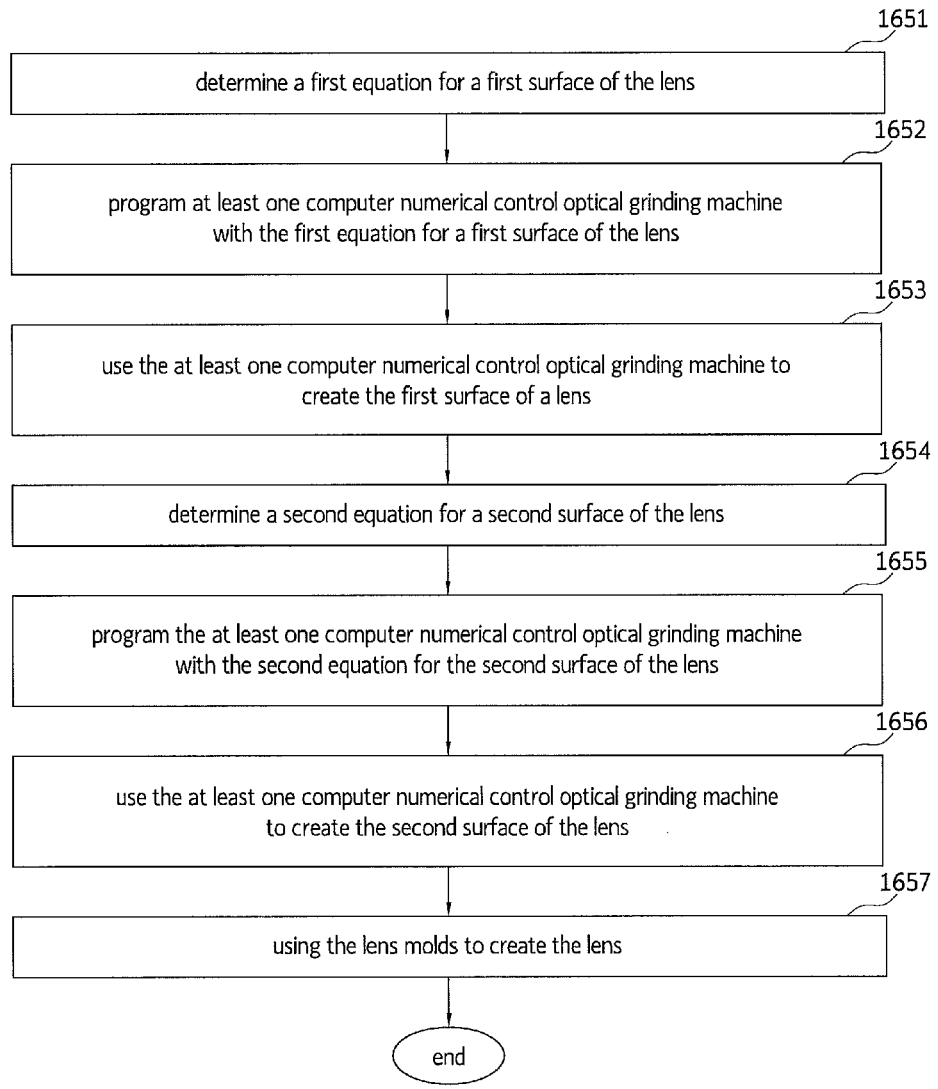
FIG. 16 illustrates a flow chart for an embodiment of a method of manufacturing eyewear.

FIG. 16 illustrates a flow chart for an embodiment of a method 1600 of method of manufacturing eyewear. Method 1600 is merely exemplary and is not limited to the embodiments presented herein. Method 1600 can be employed in many different embodiments or examples not specifically depicted or described herein. In some embodiments, the activities, the procedures, and/or the processes of method 1600 can be performed in the order presented. In other embodiments, the activities, the procedures, and/or the processes of method 1600 can be performed in any other suitable order. In still other embodiments, one or more of the activities, the procedures, and/or the processes in method 1600 can be combined or skipped.

Referring to FIG. 16, method 1600 includes an activity 1651 of determining a first equation for a first surface of the lens. In some examples, activity 1651 can include determining a first equation for the first surface of the lens wherein the first equation defines a curvature of the first surface such that the first surface has one of toroidal curvature, spherical curvature, or conical curvature.

In some examples, the first equation can define curvature of the lens such that the first surface is similar or identical to surface 120, 820, 1020, or 1230 of FIGS. 1, 8, 10, and 12, respectively. In some examples, a user can perform this procedure using a computer aided design (CAD) software program or another optical design software program.

As an example, an equation for a spherical surface could be $x^2+y^2+z^2=r^2$ where x, y and z are points sets on the surface, and r is the radius of the sphere.

In some examples, the best-fit arc surface meets the center and edge thickness. The surface can have more or less taper to start with depending if the lens designer wants to favor forward gaze (taper) or omni-directional viewing (e.g., constant thickness).

As part of activity 1651, the lens designer can determine a coordinate from which the surface can be scaled to correct the summit of this surface on the optical plane (generation plane common to both inner and outer surfaces).

In some examples, the lens designer scales the surface with independent X, Y, and Z scaling factors. Depending on these factors, the resulting surfaces can be elliptical in nature and may or may not have an axis of rotation for polishing.

In these examples, these surfaces are simple to represent in a mathematical form as to produce accurate optical surfaces that can be accurately CNC machined and polished.

In some examples, for spindle toric and the tapered conical surface, it may not be possible to rotate the ellipse around a horizontal plane to generate the elliptical correction. In various examples, a scaling approach can be used instead. In the scaling approach, the designer first creates the basic surface that is needed. Then the designer performs the XYZ scaling with different parameters on each plane to transform the surface into the elliptical form.

Method 1600 in FIG. 16 continues with an activity 1652 of programming at least one computer numerical control machine with the first equation for the first surface of the lens. In some examples, a user can program the computer numerical control machine with the equation for the first surface of the lens. In some examples, the user can transfer the equation from the computer software used to create the first equation to the computer numerical control milling machine.

Subsequently, method 1600 of FIG. 16 includes an activity 1653 of using the computer numerical control machine to create a mold for the first surface of a lens. In some examples, activity 1653 can include using the computer numerical control machine to create a mold of a first surface of a lens wherein the first surface has at least one of a toroidal curvature, a cylindrical curvature, a spherical curvature, or a conical curvature. The computer numerical control machine can create the first surface of the lens mold using the first equation for the first surface of the lens.

In some examples, molds can be generally generated by CNC (computer numeric control) programming. For example, the mold can be generated using CAM software or programming of the surface equation directly into the CNC controller for improved accuracy.

Next, method 1600 of FIG. 16 includes an activity 1654 of determining a second equation for a second surface of the lens. In some examples, activity 1654 can include determining a second equation for the second surface of the lens wherein the second equation defines a curvature of the second surface such that: (a) the second surface has the substantially elliptical curvature, (b) the lens has a first thickness at the center of the lens, (c) the lens has a second thickness at the two peripheral edges of the lens, (d) the lens has a third thickness at the point between the center of the lens and each of the peripheral edges of the lens, and (e) the lens provides the horizontal prism of substantially zero. In many examples, the first thickness is greater than the second thickness and the third thickness, and the second thickness is greater than the third thickness.

In some examples, a user can perform this procedure using a CAD software program or another optical design software program.

In a first example, an equation for an elliptical curve can be:

$$x^2/a^2 = y^2/b^2 = 1$$

where x and y are points of the curve and a and b are the major and minor axes of the curve.

In another example, the equation for a first spherical surface with an equation of:

$$x^2 + y^2 + z^2 = r^2,$$

where x, y, and z are points on the surface and r is the radius of the surface.

The equation for the second elliptical surface could be:

$$x^2/a^2 + y^2/b^2 + z^2/c^2 = 1$$

where x, y, and z are points of the curve and a, b, and c are the radii of the elliptical surface.

In various embodiments, activity 1654 can precede or be immediately subsequent to activity 1651 and before activities 1652 and 1653.

Method 1600 in FIG. 16 continues with an activity 1655 of programming the computer numerical control machine with the second equation for the second surface of the lens. In some examples, a user can program the computer numerical control machine with the equation for the second surface of the lens. In some examples, the user can transfer the equation from the computer software used to create the second equation to the computer numerical control machine. In various embodiments, activity 1655 can precede or be immediate subsequent to activity 1652 and be before activity 1653.

Subsequently, method 1600 of FIG. 16 includes an activity 1656 of using the computer numerical control machine to create a mold of the second surface of the lens. In some examples, activity 1656 can include using the computer numerical control machine to create a mold of a second surface of the lens such that: (a) the second surface has a substantially elliptical curvature, (b) the lens has the first thickness at a center of the lens, (c) the second thickness at two peripheral edges of the lens, (d) the third thickness at a point between the center of the lens and each of the peripheral edges of the lens, and (e) the lens provides a horizontal prism of substantially zero. In many examples, activity 1656 can include using the computer numerical control machine to create the second surface of the lens mold using the second equation for the second surface of the lens.

In some examples, activity 1656 can be precede, be concurrent with, or occur immediately after activity 1653.

Method 1600 in FIG. 16 continues with an activity 1657 of using the lens molds to create the lens. In some examples, the lens molds can be created using an injection molding process, a casting process, or another process.

In some examples, after creating the lens, a hard lapping process can be used to polish the first surface of the lens. In other examples, a soft lapping or another process can be used to finish the first surface of the lens.

In various embodiments, one surface can be simple (arcuate with a degree of translation or rotation) and this surface can be hard lapped to a high level of finish. One of the advantages of the embodiments described herein is that one surface can be conventionally polished to a high degree of finish and thus, in some examples, only one surface of the lens needs more treatment. The method and system described herein reduces the amount of soft lapping to the least amount possible. Using the method described herein, one of the surfaces is easily polished so the amount of money and time needed to produce the lens is reduced.

In various embodiments, the elliptically corrected surface (e.g., the first surface) can be hard lapped if there is an axis of rotation (elliptical tonic for example), or soft lapped (surfaces with no axis or rotation).

Furthermore, in some examples, a hard lapping, soft lapping, or another process can be used to polish the second surface of the lens.

After activity 1657, method 1600 is complete.

Although the invention has been described with reference to specific embodiments, it will be understood by those skilled in the art that various changes may be made without departing from the spirit or scope of the invention. Accordingly, the disclosure of embodiments of the invention is intended to be illustrative of the scope of the invention and is not intended to be limiting. It is intended that the scope of the invention shall be limited only to the extent required by the appended claims. For example, to one of ordinary skill in the art, it will be readily apparent that activities 1451 and 1452 of FIG. 14, activities 1651, 1652, 1653, 1654, 1655, 1656, and 1657 of FIG. 16, and procedures 1561, 1562, 1563, and 1564 of FIG. 15 may be comprised of many different activities and procedures, in many different orders, and that the foregoing discussion of certain of these embodiments does not necessarily represent a complete description of all possible embodiments.

All elements claimed in any particular claim are essential to the embodiment claimed in that particular claim. Consequently, replacement of one or more claimed elements constitutes reconstruction and not repair. Additionally, benefits, other advantages, and solutions to problems have been described with regard to specific embodiments. The benefits, advantages, solutions to problems, and any element or elements that may cause any benefit, advantage, or solution to occur or become more pronounced, however, are not to be construed as critical, required, or essential features or elements of any or all of the claims, unless such benefits, advantages, solutions, or elements are stated in such claim.

Moreover, embodiments and limitations disclosed herein are not dedicated to the public under the doctrine of dedication if the embodiments and/or limitations: (1) are not expressly claimed in the claims; and (2) are or are potentially equivalents of express elements and/or limitations in the claims under the doctrine of equivalents.

What is claimed is:

1. A lens for protection of one or more eyes of a user, the lens comprising:
   a first surface; and
   a second surface spaced apart from the first surface such that the lens has a variable thickness between the first surface and the second surface,
   wherein:
   the first surface comprises substantially an arc;
   the second surface comprises a substantially elliptical curve;
   the lens is a smooth, arcuate, substantially plano lens; and
   wherein the lens has a first thickness at a center of the lens;
   the lens has a second thickness at a lateral edge of the lens;
   the lens has a third thickness at a position between the center of the lens and the lateral edge of the lens;
   the first thickness is greater than the third thickness;
   the first thickness is greater than or equal to the second thickness;
   the second thickness is greater than the third thickness;
   the first surface is a first continuous optical surface; and
   the second surface is a second continuous optical surface.

2. The lens of claim 1, wherein:
   the first surface comprises at least one of a toroidal surface, a cylindrical surface, a spherical surface, or a conical surface.

3. The lens of claim 1, wherein:
   the first thickness is approximately two millimeters to approximately six millimeters;
   the second thickness is between 7/10ths to 9/10ths of the first thickness; and
   the third thickness is between 5/10ths to 8/10ths of the first thickness.

4. The lens of claim 1, wherein:
   the lens has a thickest point at a center of the lens; and
   the lens has a thinnest point between the center of the lens and an outboard edge of the lens.

5. The lens of claim 1, wherein:
   an eccentricity of the substantially elliptical curve of the second surface is between 0.001 and 0.375.

6. The lens of claim 1, wherein:
   a combination of the first surface and the second surface provides at least one of:
   a horizontal prism of substantially zero;
   a power of substantially zero; or
   astigmatism of substantially zero.

7. The lens of claim 1, wherein:
   the lens complies with an impact resistance requirement of at least one of: (a) the ANSI (American National Standard Institute) Z87.1 standard; (b) the ANSI Z87.1+ standard; (c) CSA (Canadian Standards Association) Z94.3.1 standard; (d) MILV43511 standard; (e) U.S. military MIL-STD-622 standard; (f) U.S. military MIL-PRF-31013 standard; (g) CSA Z94.3.1 standard; (h) European EN 166 standard; (i) NFPA (National Fire Protection Association) standard; (j) Canadian CAN/CSA-Z262.2-M90 standard; or (k) ASTM (American Society for Testing and Materials) F513 standard.

8. The lens of claim 1, wherein:
   the second surface comprises a substantially ellipsoidal surface; and
   the substantially ellipsoidal surface comprises the substantially elliptical curve.

9. The lens of claim 1, wherein:
   the lens is a face shield, a visor or a goggle lens.

10. Eyewear for protection of the eyes of a user, the eyewear comprising:
    a frame; and
    a unitary lens coupled to the frame, the unitary lens has a center, a first peripheral edge spaced apart from the center, a second peripheral edge spaced apart from the center and the first peripheral edge, the unitary lens comprising:
    a first surface extending from the first peripheral edge to the second peripheral edge; and
    a second surface spaced apart from the first surface and extending from the first peripheral edge to the second peripheral edge,
    wherein:
    when the eyewear is worn by the user, the first surface and the second surface of the unitary lens covers both of the eyes of the user;
    when the eyewear is worn by the user, an inner surface of the unitary lens is closer to the eyes of the user than an outer surface of the unitary lens;
    the first surface has at least one of a toroidal curvature, a cylindrical curvature, a spherical curvature, or a conical curvature;
    the second surface comprises a substantially elliptical curvature;
    the unitary lens is a smooth, substantially plano lens;
    one of the first surface and the second surface is the inner surface of the unitary lens; and
    one of the first surface and the second surface is the outer surface of the unitary lens;
    wherein:
    the unitary lens has a first thickness at the center;
    the unitary lens has a second thickness at the first peripheral edge and the second peripheral edge;
    the unitary lens has a third thickness at a first position between the center and the first peripheral edge;
    the unitary lens has a fourth thickness at a second position between the center and the second peripheral edge;
    the first thickness is greater than or equal to the second thickness;
    the first thickness is greater than the third thickness and fourth thickness;

the second thickness is greater than the third thickness and fourth thickness;

the third thickness is equal to the fourth thickness;

lens is a face shield, a visor, or a goggle lens;

the first thickness, the second thickness, the third thickness, and the fourth thickness are distances between the first surface of the unitary lens and the second surface of the unitary lens; and the first position and second position are symmetric with the center.

11. The eyewear of claim 10, wherein:

a combination of the first surface and the second surface provides at least one of:

a horizontal prism of substantially zero;

a power of substantially zero; or astigmatism of substantially zero.

12. A method of manufacturing eyewear, the eyewear comprises a lens, the method comprising:

using at least one computer numerical control machine to create a first lens mold surface of a lens mold for a first surface of a lens wherein the first surface comprises at least one of a toroidal curvature, a spherical curvature, a cylindrical curvature, or a conical curvature;

using the at least one computer numerical control machine to create a second lens mold surface for a second surface of the lens such that: (a) the second surface has a substantially elliptical curvature, (b) the lens has a first thickness at a center of the lens, (c) the lens has a second thickness at two peripheral edges of the lens, (d) the lens has a third thickness at a point between the center of the lens and each of the peripheral edges of the lens, and (e) the lens provides at least one of:

a horizontal prism of substantially zero;

a power of substantially zero; or astigmatism of substantially zero; and using the lens molds to create the lens of the eyewear, wherein:

the first thickness is greater than or equal to the second thickness;

the first thickness is greater than the third thickness; and the second thickness is greater than the third thickness.

13. The method of claim 12, further comprising:

determining a first equation for the first surface wherein the first equation defines a curvature of the first surface such that the first surface comprises one of the toroidal curvature, the spherical curvature, the cylindrical curvature, or the conical curvature;

programming the at least one computer numerical control machine with the first equation for the first surface of the lens, wherein:

using the at least one computer numerical control machine to create the first lens mold surface of a lens mold comprises:

using the at least one computer numerical control machine to create the first lens mold surface of the lens mold using the first equation for the first surface of the lens.

14. The method of claim 12, further comprising:

determining a second equation for the second surface of the lens wherein the second equation defines a curvature of the second surface such that: (a) the second surface has the substantially elliptical curvature, (b) the lens has the first thickness at the center of the lens, (c) the lens has the second thickness at the two peripheral edges of the lens, (d) the lens has the third thickness at the point between the center of the lens and each of the two peripheral edges of the lens, and (e) the lens provides at least one of:

a horizontal prism of substantially zero;

a power of substantially zero; or astigmatism of substantially zero; and using the lens molds to create the lens of the eyewear; and programming the at least one computer numerical control machine with the second equation for the second surface of the lens mold, wherein:

using the at least one computer numerical control machine to create the second lens mold surface comprises:

using the at least one computer numerical control machine to create the second lens mold surface of the lens molds using the second equation for the second surface of the lens.

* * * * *